US007285393B2

(12) United States Patent
Beher

(10) Patent No.: US 7,285,393 B2
(45) Date of Patent: Oct. 23, 2007

(54) ASSAY FOR MODULATION OF γ SECRETASE

(75) Inventor: D. Beher, Sawbridgeworth (GB)

(73) Assignee: Merck Sharp & Dohme Limited, Hoddesdon, Hertfordshire (GB)

( * ) Notice: Subject to any disclaimer, the term of this patent is extended or adjusted under 35 U.S.C. 154(b) by 410 days.

(21) Appl. No.: 10/739,485

(22) Filed: Dec. 18, 2003

(65) Prior Publication Data

US 2004/0132114 A1 Jul. 8, 2004

(30) Foreign Application Priority Data

Dec. 19, 2002 (GB) ................................ 0229582.2

(51) Int. Cl.
*G01N 33/53* (2006.01)

(52) U.S. Cl. .................................................... 435/7.92

(58) Field of Classification Search ..................... None
See application file for complete search history.

(56) References Cited

FOREIGN PATENT DOCUMENTS

WO WO 01/075435 10/2001
WO WO 2003/008635 1/2003

OTHER PUBLICATIONS

Evin et al. Biochemistry, 2001, 40, 8359-8368.*
Yu et al. Nature, 2000, 406, 48-54.*
Francis et al. Dev Cell, 2002, 3, 85-97.*
Li et al. Nature, 2000, 405, 689-694.*
D. Beher et al., "InVitro Characterization of the Presenilin-Dependent Gamma-Secretase Complex Using a Novel Affinity Ligand", Biochemistry, vol. 42, pp. 8133-8142 (2003).
A. Kornilova et al., "Differential Effects of Inhibitors on the Gamma-Secretase Complex", The Journal of Biological Chemistry, vol. 278, No. 19, pp. 16470-16473 (2003).
A. Weihofen et al., "Targeting Presenilin-type Aspartic Protease Signal Peptide Peptidase with Gamma-Secretase Inhibitors", The Journal of Biological Chemistry, vol. 278, No. 19, pp. 16528-16533 (2003).
I. Pinnix et al., "A Novel Gamma-Secretase Assay Based on Detection of the Putative C-terminal Fragment-Gamma of Amyloid Beta Protein Precusor", The Journal of Biological Chemistry, vol. 276, No. 1, pp. 481-487 (2001).

* cited by examiner

*Primary Examiner*—Ralph Gitomer
*Assistant Examiner*—Bin Shen
(74) *Attorney, Agent, or Firm*—John C. Todaro; Melvin Winokur

(57) ABSTRACT

There is provided an assay for identifying compounds which interact with the γ-secretase complex, in particular compounds that lower the production of Aβ42.

13 Claims, 10 Drawing Sheets

Figure 5a and b
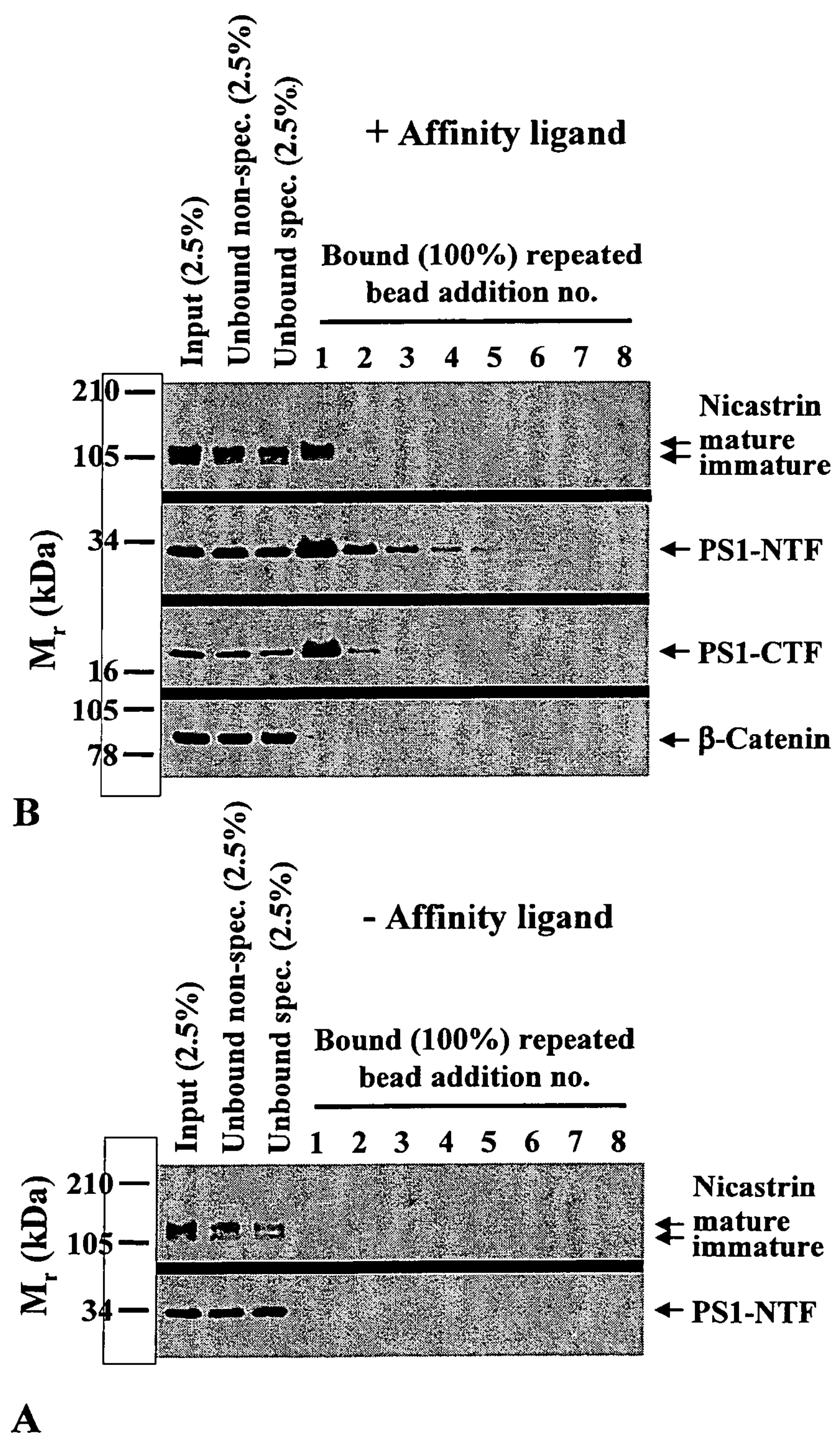

ASSAY FOR MODULATION OF γ SECRETASE

CROSS REFERENCE TO RELATED APPLICATIONS

This application claims priority under 35 U.S.C. § 119 from GB Application No. 0229582.2, filed Dec. 19, 2002.

The present invention relates to an assay for identifying compounds which interact with the γ-secretase complex. In particular the assay identifies compounds which increase the affinity of the complex for certain probes.

Alzheimer's Disease (AD) is believed to result from the deposition of quantities of a peptide, amyloid-β (Aβ), within the brain. This peptide is produced by enzymatic cleavage of β-amyloid protein precursor (βAPP) protein. The C-terminus of Aβ is generated by an enzyme termed γ-secretase. Cleavage occurs at more than one site on βAPP producing different length Aβ peptides, some of which are more prone to deposition, such as Aβ42. It is believed that aberrant production Aβ42 in the brain leads to AD (for review see Hardy and Selkoe, 2002). It is thus desirable to seek inhibitors of the production of this Aβ peptide.

Inhibitors may function in a variety of ways. They may block γ-secretase completely, or they may alter the activity of the enzyme so that less Aβ42 and more of the alternative, soluble, forms of Aβ, such as Aβ38 are produced. Such inhibitors may thereby retard or reverse the development of AD.

The nature of the γ-secretase complex is only partly characterised. It is believed to be a complex of at least four proteins: presenilin 1 (PS 1) (Rogaev et al., 1995; Sherrington et al., 1995; Li et al., 2000b) which mainly occurs as a heterodimer of its N- and C-terminal fragment (PS1-NTF and PS1-CTF) generated by endoproteolysis of the full-length polypeptide (PS1-FL) within its putative loop region (Thinakaran et al., 1996), nicastrin (Yu et al., 2000; Esler et al., 2002; Kimberly et al., 2002) APH-1 and PEN-2 (Francis et al., 2002; Steiner et al., 2002; Lee et al., 2002).

γ-Secretase has more than one enzymatic activity cleaving multiple substrates. It is also involved in processing the Notch receptor, part of a signalling pathway critical for embryonic development. The importance of this pathway is seen in knockout PS-1 mice which die in utero or shortly after birth (Shen et al., 1997;Wong et al., 1997). It is thus desirable to be able to identify compounds which interact with γ-secretase to reduce the production of Aβ42 without preventing or interfering with the ability of γ-secretase to process Notch.

Compounds are known, such as indomethacin, ibuprofen and sulindac sulphide, which inhibit the production of Aβ42 whilst increasing the production of Aβ38 and leaving the production of Aβ40 constant (Weggen et al., 2001). However such compounds must be identified by laboriously measuring the amount of various forms of Aβ produced in γ-secretase preparations or cells with which the compounds are incubated.

The applicants have surprisingly found that incubation of a source of γ-secretase together with an affinity probe, as defined below, can be used to determine whether test compounds interact with the enzyme. In particular this is achieved by analysing the components of the enzyme captured by the affinity probe and comparing with control. It has been found, surprisingly, that certain compounds increase the amount of γ-secretase complex captured by the affinity probe. Such compounds are believed to have the advantageous properties of lowering the production of Aβ42, raising the production of Aβ38 and leaving the production of Aβ40 unchanged. The assay can also be used to identify compounds which compete with the affinity probe: in such cases the probe will capture fewer components than control.

It is hypothesised this surprising finding may be explained by the fact that γ-secretase is an aspartyl protease: both PS1-NTF and PS-CTF contain aspartyl residues critical for γ-secretase activity in their putative transmembrane domains (Wolfe et al., 1999). In common with other aspartyl proteases it is believed that γ-secretase can assume alternative conformations. It may be that certain conformations will process βAPP differently. Thus if compounds can be identified which lock the complex into a particular conformation, the production of insoluble Aβ could be reduced. It is thought that the affinity probe binds to a particular conformation of the γ-secretase complex. If a test compound locks the enzyme into this conformation the affinity probe will bind to more of the enzyme and this can be detected by measuring the amount of PS1-CTF, PS1-NTF and/or nicastrin captured by the affinity probe. It is understood that the conformation of the enzyme to which the affinity probe binds cleaves βAPP processing intermediates to produce Aβ38 in place of Aβ42 hence the assay is indicative of the ability of a test compound to decrease the production insoluble Aβ from βAPP.

DETAILED DESCRIPTION OF THE INVENTION

Figure 1:
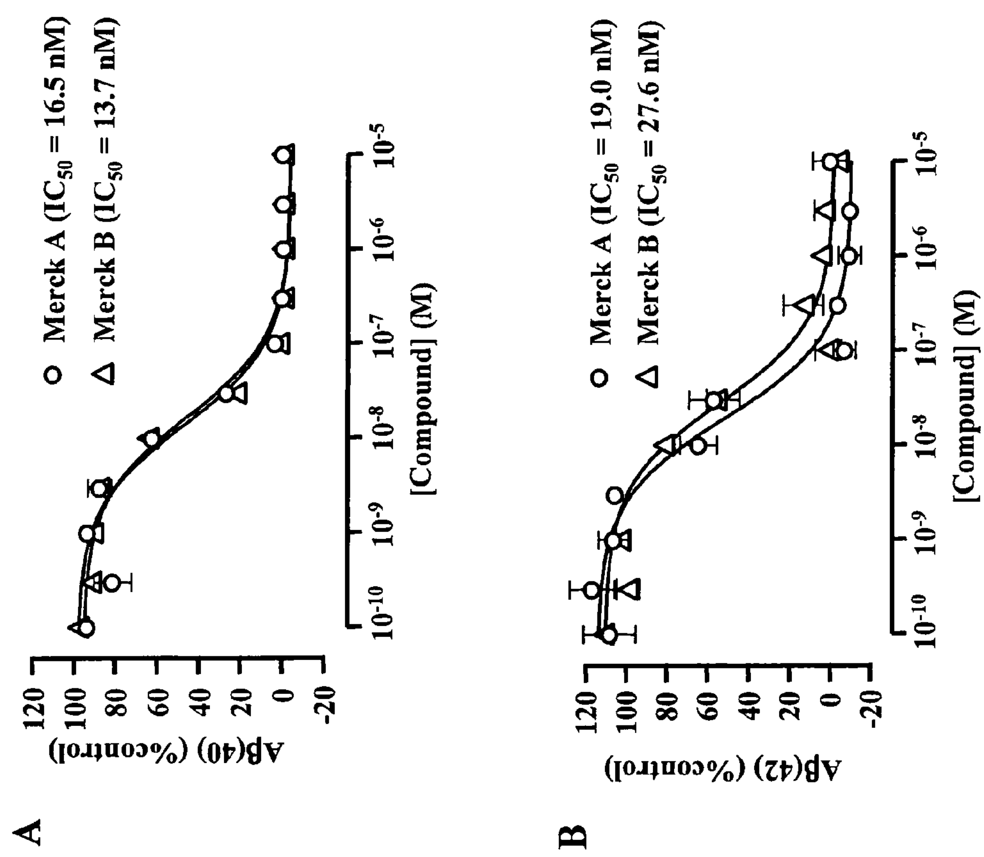
FIGS. 1A & 1B γ-Secretase inhibitors synthesized for this study and their potencies for inhibition of γ(40)- and γ(42)-secretase activities FIGS. 2A & 2B Affinity capture of PS1 heterodimer and nicastrin by the biotinylated inhibitor Merck C FIGS. 3A & 3B The binding of PS1 heterodimer and nicastrin to the biotinylated affinity probe is competed by the non-biotinylated inhibitor Merck A FIG. 4. Simultaneous binding of the substrate and a transition state analogue inhibitor to γ-secretase FIGS. 5A, 5B & 5C Quantitation of the depletion of γ-secretase activity from solubilized membranes by binding to the biotinylated affinity probe FIG. 6 Subcellular fractionation of γ-secretase FIG. 7. The binding of the PS1 heterodimer and nicastrin to the biotinylated affinity probe is enhanced by the selectively Aβ(x-42)-lowering compound sulindac sulphide
Figure 2A:
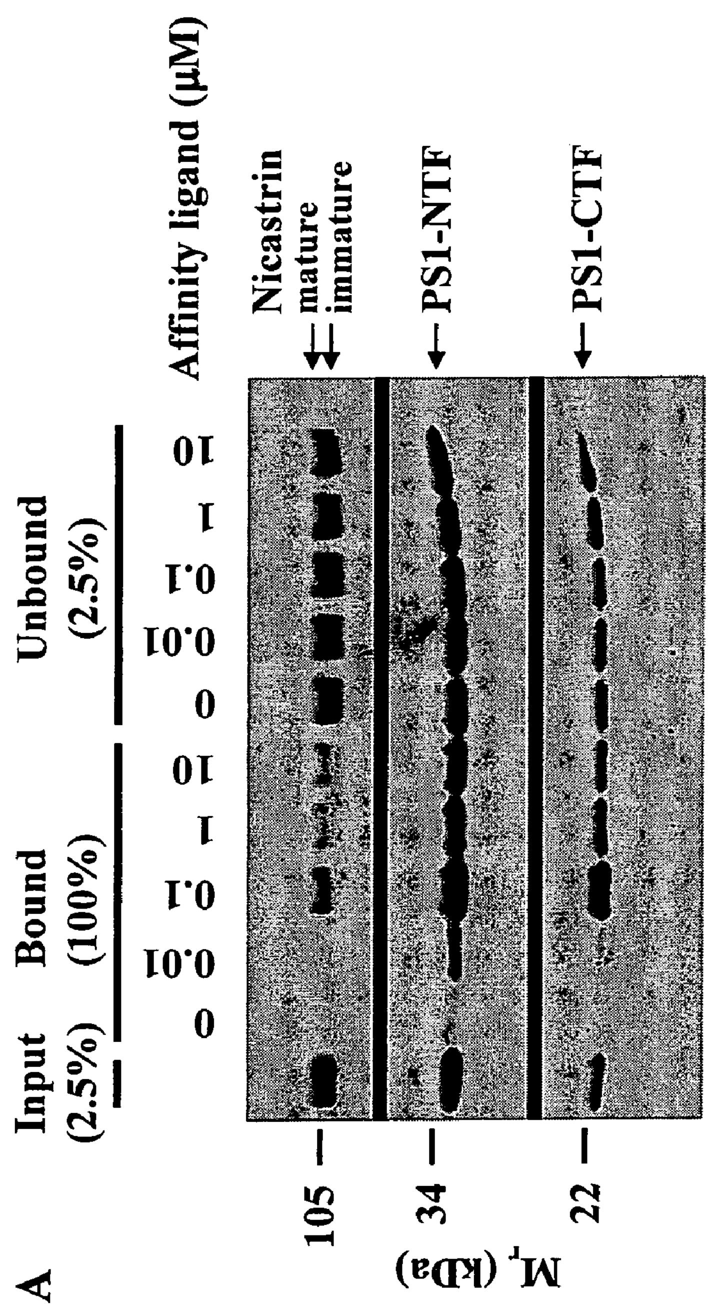
Figure 2B:
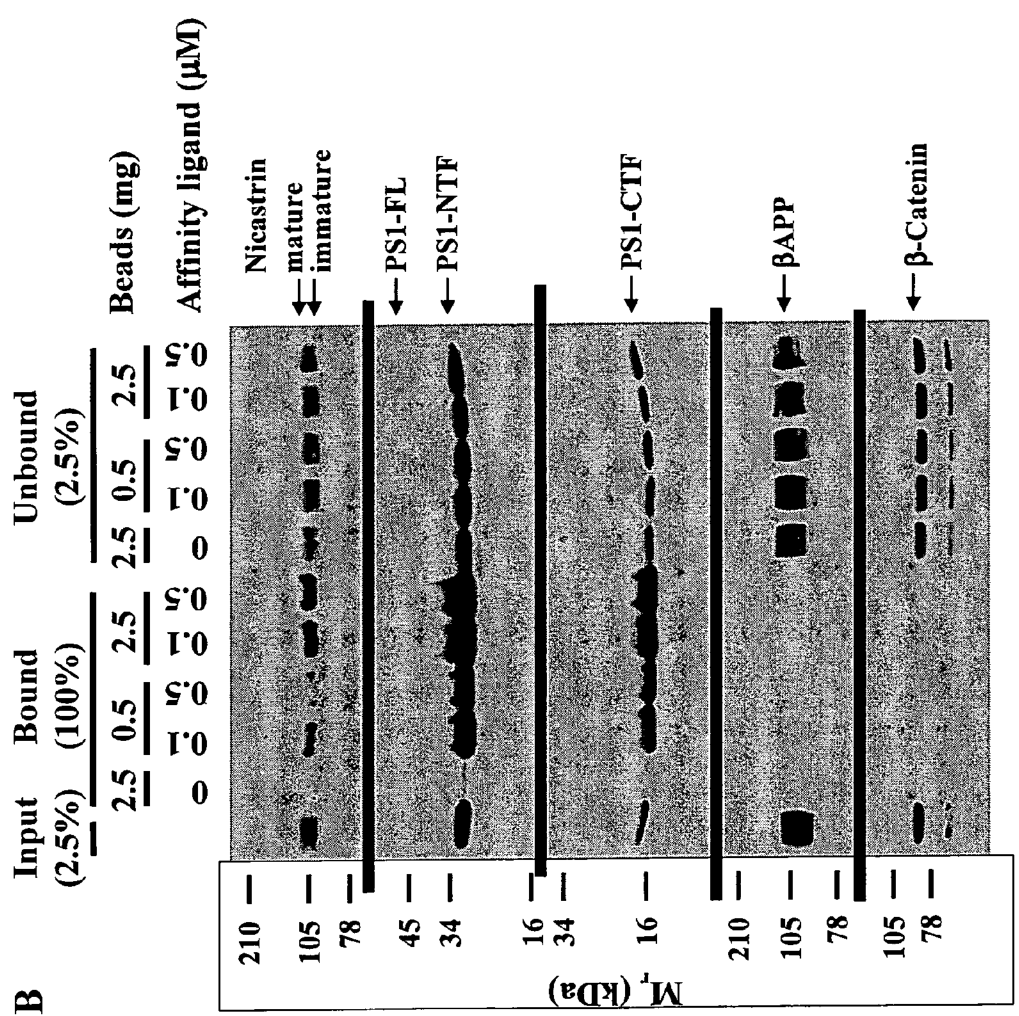

The present invention provides an assay for identifying compounds which interact with the γ-secretase complex which comprises:

preparing a biochemical source of the γ-secretase complex;

solubilizing the source;

incubating a test compound together with an affinity probe and the source;

capturing the resulting bound complex; and analysing the components of the bound complex to determine whether the test compound has interacted with the complex by assessing whether the amount of PS1-CTF, PS1-NTF or mature nicastrin bound is altered compared to control.

In one embodiment compounds are detected which diminish binding of the probe to the complex, i.e. they are competitive inhibitors with the probe for γ-secretase. In another embodiment, which is preferred, compounds are detected which enhance binding to the complex. Such compounds are thought to act by fixing the complex into a particular conformation or altering its conformation so that βAPP processing intermediates are cleaved to produce soluble Aβ38 rather than insoluble Aβ42 while not affecting the activity of the complex on Notch. Such compounds are potentially useful for treating AD without possessing deleterious side-effects resulting from blocking the activity of γ-secretase on Notch.

In a particular embodiment, the amount of two or more of the bound components PS1-CTF, PS1-NTF and mature nicastrin are measured.

The assay can also include analysis of PEN-2 and/or APH-1.

γ-Secretase complex can be prepared from a range of biochemical sources such as HEK cells, human SH-SY5Y neuroblastoma cells or brains of rodent species, such as rat or mouse, or other species such as guinea-pig, by methods known in the art. The source can include transgenic cell lines or animals which overexpress known components of the γ-secretase complex. For example, cells can be prepared, collected in a suitably buffered saline and then hypotonically shocked to lyse the cells, for example by incubating with hypotonic HEPES buffer for about 8 min. The cells are then homogenized and centrifuged to remove debris before being sedimented by further centrifugation. The sediment is then resuspended.

In one embodiment the complex is enriched (i.e. partially purified) by subcellular fractionation (e.g. sucrose density gradient centrifugations) before solubilization or by other biochemical means such as chromatography after solubilization.

A range of solubilization methods are known in the art. A preferred method utilises 1% CHAPSO (3-[(3-cholamidopropyl)dimethylammonio]-2-hydroxy-1-propanesulfonate). Insoluble debris is removed by centrifugation and the resulting supernatant is collected. In a preferred embodiment the supernatant is two-fold diluted before further use, which provides a γ-secretase complex with high catalytic activity and therefore a complex in a preferred conformation.

The affinity probe of use in the present invention can be any γ-secretase inhibitor which is labelled for detection. One particular label is biotin which, when attached, generally via a linker, to γ-secretase inhibitors can be captured by streptavidin (magnetic) beads. A particularly favoured class of inhibitors is disclosed in WO-A-0153255. Other inhibitors may be identified by the method disclosed therein.

The following compounds are referred to in the Examples.

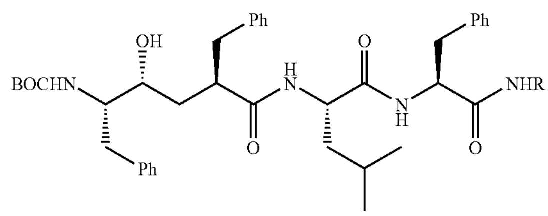

Merck A: R = H
Merck B: R = $(CH_3)_5[NHCO(CH_2)_5]_3NH_2$
Merck C: R = $(CH_2)_5[NHCO(CH_2)_5]_3NHCO(CH_2)_2S\text{–}S\text{–}(CH_2)_2NH$-Biotin Merck A is a γ-secretase inhibitor disclosed in WO-A-0153255. Merck B is an affinity probe precursor disclosed in US 2002-0013276. Merck C is the preferred affinity probe used in the present invention. Its preparation is described in the Examples.

The enzyme-inhibitor complex can be recovered by conventional means, such precipitating the complex by centrifugation. The enzyme-inhibitor complex can then be analysed by conventional means such as Western blotting, which is preferred, or mass spectrometry.

The results of the analysis can be compared with control for the amounts of PS1-NTF, PS1-CTF and/or nicastrin, and optionally PEN-2 and APH-1, in the enzyme-inhibitor complex. A test compound which causes more of the γ-secretase complex to be bound is considered potentially useful for altering the activity of the γ-secretase complex to produce less insoluble Aβ42 and more soluble Aβ38 whilst not affecting activity at Notch. A compound which diminishes the amount of γ-secretase complex identified is potentially useful as a specific inhibitor of the complex.

The assay can also be used to identify further components of the γ-secretase complex. A compound which enhances amount of enzyme bound in the enzyme-inhibitor complex, such as sulindac sulphide, can be used in the assay. The enzyme-inhibitor complex can then be analysed to determine whether any components are present additional to those already known to be part of the γ-secretase complex. Such additional components can then be used to identify novel compounds which bind to them and thus are potentially useful therapies for treating Alzheimer's Disease.

The following examples illustrate the invention.

EXAMPLE 1

Experimental Procedures

Materials—Monoclonal antibodies and polyclonal antisera were obtained from the following sources and diluted for Western blot analyses as indicated: anti-βAPP (22C11, Chemicon, 0.5 μg/ml), anti-calnexin (StressGen, 1:2,500), anti-β-catenin (BD Transduction Laboratories, 1:1,000), anti-β-COP (Sigma, 1:500), anti-syntaxin 6 (BD Transduction Laboratories, 1:500), anti-rab6 (Autogen Bioclear, 1:500), biotinylated anti-Aβ 4G8 (Senetek), HRP-conjugated polyclonal goat anti-mouse and anti-rabbit antibodies (Amersham, 1:5,000), and polyclonal rabbit antiserum R7334 (raised against residues 659–694 of $\beta APP_{695}$, 1:750). PS1-FL and its fragments were detected using the polyclonal rabbit antisera 00/2 raised against the loop peptide 301–317 (Evin et al., 2001) (1:2,000) and 98/1 raised against residues 1–20 of PS1 (1:2,500) (Culvenor et al., 2000). Polyclonal rabbit antiserum 00/19 against nicastrin was raised against a commercially synthesized peptide comprising the C-terminal residues 691–709 of human nicastrin which was coupled to diphtheria toxoid prior to the immunizations.

Western blot analyses—Equal amounts of protein were separated by SDS-polyacrylamide gel electrophoresis and transferred to nitrocellulose membranes. Probing of the membranes was carried out with various antibodies, as indicated in the figures, using the enhanced-chemiluminescence system (ECL, Amersham). Quantitation of bands using a computerized image analysis system (MCID, Imaging Research Inc.) was performed as described previously (Beher et al., 1999).

Membrane preparation—Membranes from human SH-SY5Y neuroblastoma cells were prepared essentially as described previously (Beher et al., 2001). Briefly, after collection in phosphate buffered saline (PBS), 2 mM EDTA cells were hypotonically shocked by incubation for 8 min in 20 mM HEPES-HCl, pH 7.3, 10 mM KCl and sedimented by centrifugation for 10 min at 1,000 g. Cells were homogenized in 20 mM HEPES-HCl, pH 7.3, 90 mM KCl and nuclei and cellular debris removed by centrifugation for 10 min at 1,000 g. Cellular membranes were sedimented by centrifugation for 1 h at 45,000 rpm (50.2 Ti rotor, Beckman), resuspended in PBS, 5% glycerol and stored at −80° C. prior to further use.

Subcellular fractionation and sucrose density gradient centrifugation—Human SH-SY5Y neuroblastoma cell membranes were prepared as described above and separated on a linear continuous sucrose gradient (0.2–2M) according to (Beher et al., 2001). Fractions were collected (17×1.0 ml) from the bottom, diluted into 5 mM HEPES-HCl, pH 7.3, and membranes sedimented by centrifugation at 45,000 rpm (50.2 Ti rotor, Beckman) for 1 h. The final pellets were homogenized in 400 μl PBS, 5% glycerol (v/v) and stored at −80° C. prior to immunoblot analysis or in vitro γ-secretase assays.

CHAPSO-solubilization of active γ-secretase and inhibitor affinity precipitations—SH-SY5Y membranes stored in PBS, 5% glycerol were collected by centrifugation for 30 min at 180,000 g. Membrane proteins were solubilized in 1% (w/v) CHAPSO, 50 mM MES-NaOH, pH 6.0, 0.15 M NaCl, 5 mM $MgCl_2$, 1×EDTA-free protease inhibitor mixture (Roche Molecular Biochemicals). Insoluble debris was removed by centrifugation at 180,000 g for 30 min and the resulting supernatant (solubilized γ-secretase) adjusted with the same buffer without CHAPSO to give a final detergent concentration of 0.5% CHAPSO (w/v). Endogenous biotinylated proteins were removed by adding streptavidin-coupled magnetic beads and centrifugation for 2 min at 20,000 g after an incubation for 30 min at 4° C. For specific capture the pre-cleared solubilized preparation (1.8 ml; 0.6–0.7 mg/ml protein) was incubated for 2 h at room temperature with the biotinylated aspartyl transition state analogue inhibitor Merck C at the concentrations indicated in the figure legends. Non-specific binding was analysed either by omitting the biotinylated affinity ligand or adding a 100-fold excess of the non-biotinylated inhibitor Merck A. γ-Secretase-inhibitor complexes were captured by addition of 250 μl (10 mg/ml) of streptavidin-coupled magnetic beads (Dynal) and incubation for 0.5 h at room temperature. Enzyme-inhibitor complexes were precipitated by centrifugation, the beads washed three times with corresponding buffer (0.5% CHAPSO) and subjected to immunoblotting as described (Beher et al., 2001) after addition of SDS-PAGE sample buffer. Note that routinely the precipitate was split into three samples for Western blot analysis. By considering these individual samples as 100%, the precipitate (100%) was compared to 2.5% of either the input before capture or the remaining unbound fraction after capture.

Exogenous substrate γ-secretase assays—For determination of the potencies of Merck A and B, membranes from SH-SY5Y membranes stored in PBS, 5% glycerol were collected by centrifugation for 30 min at 180,000 g. For in vitro generation of Aβ peptides, 80 μg of membranes were incubated with 7.5 μg of recombinant C100Flag (Li et al., 2000a) in 20 mM HEPES, pH 7.3, 2 mM EDTA, 0.1% bovine serum albumin, 0.5% CHAPSO in 100 μl final volume similar to described methods (Li et al., 2000a) in the presence of increasing compound concentrations. Aβ peptides were quantified by an electrochemiluminescence assay in a 96-well plate format [Origen M-Series™ analyzer, Igen] as described (Beher et al., 2001) using 35 μl of the reaction for Aβ(40) and 50 μl for Aβ(42) detection. Non-specific background was defined by the signal obtained when the assay was performed in the presence of 10 μM of Merck A. For determination of γ-secretase activity in the sucrose gradient fractions, 20 μl of each fraction were incubated with 10 μg of recombinant C100Flag and processed further as above.

Synthetic chemistry—A solution of $BOCNH(CH_2)_5NHCO(CH_2)_5NH_2$ (1.1 g), $HO_2C(CH_2)_5NHCO(CH_2)_5NHFMOC$ (1.5 g), EDC (0.86 g) and HOBT (0.61 g) in DMF (20 ml) was stirred at room temperature for 5 d. The reaction mixture was diluted with ethyl acetate, and washed with citric acid solution, sodium bicarbonate solution and brine. A white precipitate formed, which was collected by filtration and washed with water and ether several times and dried in vacuo to give the tripeptide (1.9 g, 77%). The resulting tripeptide (1.0 g) was dissolved in 10% TFA-DCM and stirred overnight. The reaction mixture was evaporated in vacuo and purified by column chromatography to give the amine (1.0 g, ca 100%) as a white powder. This was dissolved in DMF (15 ml) and treated with Leu-Phe-$NH_2$ (0.82 g), EDC (0.48 g), HOBT (0.34 g) and stirred for 72 h. The reaction mixture was diluted with ethyl acetate and brine. A white precipitate formed, which was collected by filtration and washed with water and ether and dried in vacuo to give the corresponding pentapeptide (0.8 g). This was dissolved in 20% TFA-DCM and stirred for 2 h. The reaction mixture was evaporated in vacuo and purified by flash column chromatography to give the amine (500 mg, 31%) as a white solid. This was dissolved in DMF (10 ml) and treated with 2R-benzyl-5S-tert-butoxycarbonylamino-4R-(tert-butyldimethylsilanyloxy)-6-phenyl-hexanoic acid (Nadin et al., 2001) (0.31 g), EDC (134 mg) and HOBT (95 mg) and stirred overnight. The reaction mixture was diluted with ethyl acetate, and washed with citric acid solution, sodium bicarbonate solution and brine, dried ($MgSO_4$), filtered and evaporated in vacuo. Purification by flash column chromatography gave the hexapeptide (700 mg, 90%) as a white powder. The hexapeptide (350 mg) was dissolved in TBAF (1.0 M in THF, 3 ml) and stirred for 2 d. The reaction mixture was evaporated in vacuo, purified by column chromatography on silica and further by reverse-phase HPLC to give Merck B (50 mg).

A solution of Merck B (10 mg) was treated with EZ-LINK™ Sulfo-NHS-SS-Biotin (Pierce) (1 equivalent), triethylamine (1 equivalent) and stirred overnight. Addition of water and ether caused formation of a precipitate, which was filtered and washed with ether and water to give Merck C (9.6 mg, 78%) as a white solid. The synthesis of Merck A has been described previously (Shearman et al., 2000).

Results

Development of a biotinylated γ-secretase affinity ligand—To develop a novel soluble γ-secretase affinity ligand we synthesized Merck B, a derivative of our well-characterized affinity ligands (Li et al., 2000b) with an extended linker and a free amine functionality allowing further derivatization. Essentially, this compound represents an extended version of Merck A, a potent and selective γ-secretase inhibitor (Shearman et al., 2000) containing a hydroxyethylene dipeptide isostere. This group is known to mimic one of the two hydroxyl groups of the gem-diol transition state of aspartyl protease substrates. The inhibitor potencies of Merck B and its parent compound Merck A were compared for inhibition of γ(40)- and γ(42)-secretase activities in the exogenous substrate enzyme assay (Li et al., 2000a) (FIGS. 1, A and B). The data reveal that Merck A and Merck B are both potent inhibitors of γ(40)- and γ(42)-secretase activities with $IC_{50}$ values in the low nanomolar range. In good accordance with previous observations using a variety of specific inhibitors in cell-based assays (Beher et al., 2001), the actual potencies for inhibition of both γ-secretase activities are comparable. Merck B was used as an intermediate to synthesize the biotinylated affinity ligand Merck C by coupling of its primary amine to a thiol-cleavable linker with a biotin moiety attached. Since the detection of the Aβ peptides generated in the γ-secretase enzyme assay depends on their capture by a biotinylated antibody, it was predictable that Merck C would compete in this assay and therefore we did not evaluate this derivative under these conditions. The structure-activity relationship (SAR) for this inhibitor series, however, indicates clearly that C-terminal extensions at the peptide moiety are well tolerated, as demonstrated by the high potencies of Merck B (FIG. 1) and similar biotinylated photoaffinity probes described previously (Li et al., 2000b).

Figure 3A:
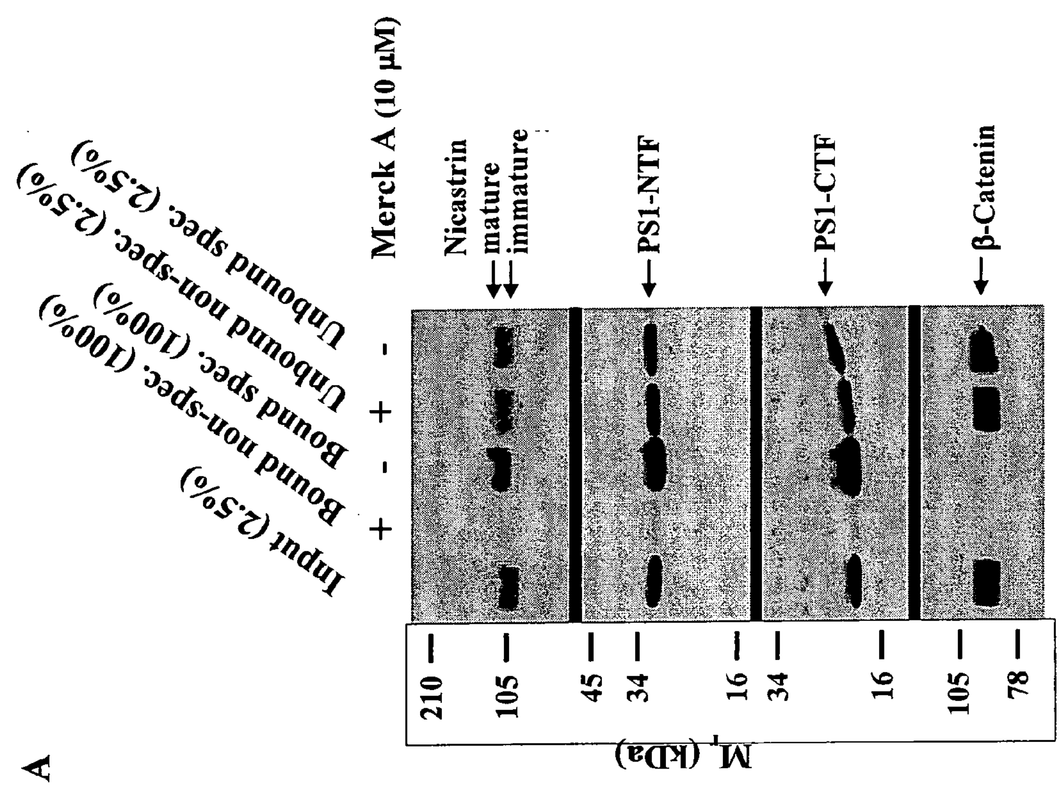
Figure 3B:
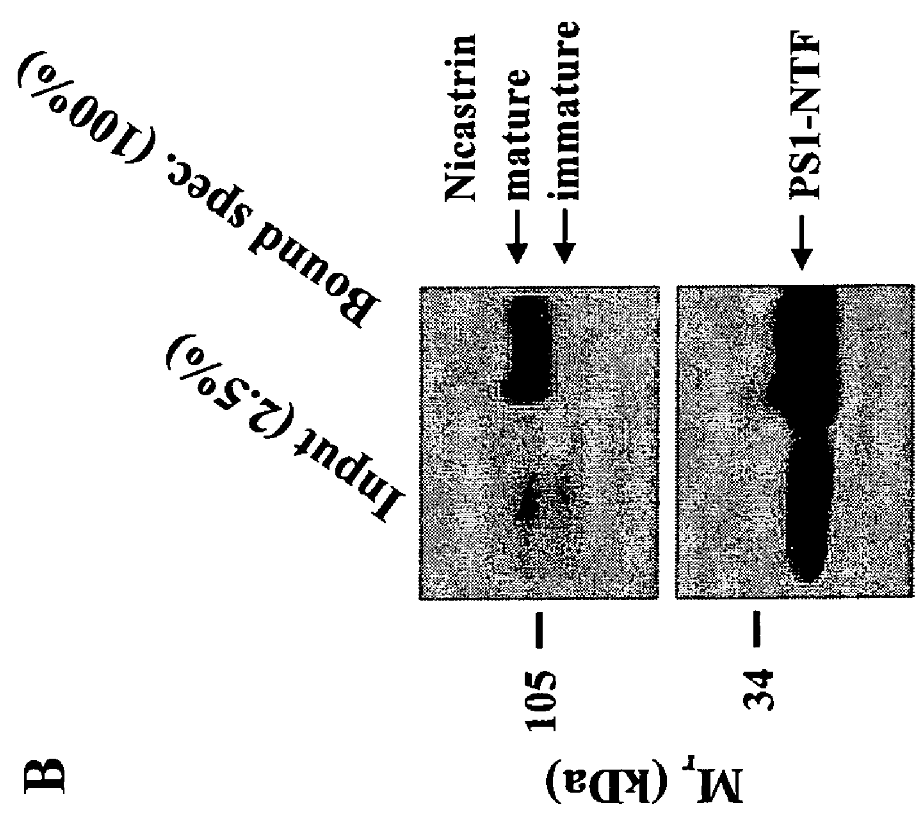

Merck C captures the PS1 heterodimer and mature nicastrin—To determine the potential of Merck C to capture solubilized γ-secretase we optimized the parameters for capture of PS1 fragments which are according to current knowledge the most likely candidate for the active site of the enzyme (Li et al., 2000b; Esler and Wolfe, 2001; Fortini, 2002). CHAPSO-solubilized -secretase from human SH-SY5Y neuroblastoma cell membranes was incubated with the biotinylated affinity ligand Merck C followed by precipitation of enzyme-inhibitor complexes with streptavidin-coupled magnetic beads. Polypeptides present in the precipitates (“Bound”) and the corresponding supernatants (“Unbound”) were characterized by Western blotting. Optimal capture conditions were determined empirically, as those yielding the most efficient captures when γ-secretase was solubilized at pH 6.0 and precipitated by streptavidin-coupled magnetic beads (as these beads appeared to show the lowest non-specific binding when compared to alternative matrices such as streptavidin-agarose beads; D. Beher, unpublished observation). Further analysis revealed that by combining an incubation of solubilised γ-secretase at an affinity ligand concentration of 0.1 μM followed by capture using 2.5 mg of magnetic beads (FIGS. 2, A and B) an optimal specific precipitation of PS1 fragments and nicastrin was observed. Omission of the affinity ligand (FIGS. 2, A and B) abolished the precipitation of all these polypeptides. Using the optimized conditions neither β-catenin nor βAPP were captured specifically (FIG. 2B), since these proteins were essentially undetectable in precipitates and only observed in the corresponding input and unbound fractions. To provide additional proof of the capture specificity, a similar affinity capture experiment was performed using the affinity ligand Merck C (0.1 μM) in the presence or absence of a 100-fold excess Merck A (10 μM) (FIG. 3A). Again both PS1 fragments and nicastrin were specifically precipitated whereas β-catenin was not detected in these fractions, only being found in the input and unbound fractions. In the presence of an excess of Merck A, PS1-NTF and PS1-CTF and nicastrin immunoreactivities were virtually undetectable in the bound fractions (FIG. 3A, “Bound non-spec.”). This result implies that either omission of the affinity ligand or addition of an excess of Merck A can serve as an appropriate control for non-specific capture. Furthermore, a selective precipitation of mature nicastrin was observed as highlighted in FIG. 3B and seen essentially in all capture experiments (FIGS. 2A–5B). Whereas two nicastrin bands migrating at ~108 kDa and ~100 kDa were detected in the input fraction, only the higher molecular weight band (~108 kDa) was captured specifically by the affinity ligand. It is noteworthy that recent studies indicate that both mature and immature forms of nicastrin carry N-linked oligosaccharides and differences in the migration could be caused by differential maturation of the N-glycan chains (Leem et al., 2002; Yang et al., 2002).

Simultaneous binding of Merck C and the substrate to the γ-secretase enzyme—Recent affinity precipitations studies using an immobilized inhibitor (Esler et al., 2002) suggest that substrate binding site(s) and active center(s) of the enzyme are not identical. To test this further we repeated the capture experiments using membranes prepared from SH-SY5Y cells stably over-expressing the y-secretase substrate SPA4CT, an artifical β-CTF (C99) variant (Dyrks et al., 1993). Again a specific capture of PS1 fragments and nicastrin was observed (FIG. 4). β-CTF accumulates as the predominant γ-secretase substrate in these membranes and consequently β-CTF was precipitated specifically by the affinity ligand. It is noteworthy, that the affinity ligand did not bind to PS1-FL (FIG. 4) as seen by its complete absence in the bound fraction.

Only a discrete fraction of PS1 is captured with active γ-secretase—Considering the results obtained with the affinity ligand (FIG. 2–4) there appears to be a low overall capture efficiency. Using this approach neither an obvious depletion of PS1-NTF and PS1-CTF nor nicastrin immunoreactivities was observed in the corresponding supernatants of the captures (“Unbound”) when compared to the original input. Furthermore, considering that the Western blot analyses compare 100% of the bound fractions to 2.5% of the input/unbound fractions there appears to be a specific capture representing ~10% of total PS1 (densitometry of PS1-NTF and PS1-CTF lanes; mean of all experiments shown in FIG. 2B–FIG. 4). In order to investigate this further, we sought to quantitate the depletion of γ-secretase enzyme activity in the corresponding supernatants following affinity precipitation. After formation of enzyme-inhibitor complexes, the samples were treated with a total of eight repeated additions of streptavidin beads followed by precipitation to remove any free affinity ligand. As shown (FIGS. 5, A and B) with an increased number of repeated bead additions PS1-NTF, PS1-CTF and nicastrin immunoreactivities decreased in the bound fraction to undetectable levels. This indicates the efficient removal of the affinity ligand. When the final supernatant (after eight repeated captures) was assayed for γ-secretase enzyme activity a ~70% decrease of both γ(40)- and γ(42)-secretase activity was observed (FIG. 5C). Taken together, these data imply that ~10% of the total PS1 captured appears to account for ~70% of the total γ-secretase enzyme activity. This indicates that only a discrete fraction of total cellular presenilin and nicastrin molecules are present in the active enzyme complex. Furthermore, as expected from the inhibitor profiling data (FIG. 1) a single specific affinity ligand binds both to γ(40)- and γ(42)-secretase which suggests that these activities are mediated by the same molecular entity.

Subcellular distribution of γ(40)- and γ(42)-secretase activity—To investigate whether the above finding is supported by the subcellular distribution of both γ-secretase activities, γ(40) and γ(42), membranous organelles from SH-SY5Y neuroblastoma cells were separated by sucrose equilibrium density gradient centrifugation. The distribution of γ(40)- and γ(42)-secretase activity across the gradient was measured by de novo production of Aβ peptides from the recombinant substrate C100Flag in individual fractions and directly compared to known marker proteins (as detected by Western blotting) (FIGS. 6, A and B). β-COP is a COP-I coatamer component required for transport between ER and Golgi (Pepperkok et al., 1993) and resides mainly in the ER-Golgi intermediate compartment (ERGIC) (Griffiths et al., 1995; Klumperman et al., 1998b) and early Golgi compartments such as cis-Golgi (Pepperkok et al., 1993). Rab6 is a ubiquitous small GTPase associated with the membranes of medial- and trans-Golgi (Goud et al., 1990; Antony et al., 1992) and has been implicated in intra-Golgi transport (Martinez et al., 1994) and a novel Golgi/ER retrograde pathway (White et al., 1999; Girod et al., 1999). Although PS1-NTF and PS1-CTF immunoreactivities (FIG. 6B) and γ(40)- and γ(42)-secretase enzyme activity (FIG. 6A) could be detected across the gradient, the actual peaks were dissimilar to those of the marker proteins of the earlier biosynthetic organelles such as the ER marker calnexin, ERGIC marker β-COP and medial-/trans-Golgi marker rab6. In contrast to this, peaks for γ(40)- and γ(42)-secretase activity and PS1 fragments tracked the distribution of syntaxin 6 (FIGS. 6, A and B, fractions 8–11, highlighted box). Overall this suggests an enrichment of γ-secretase enzyme activity in the trans-Golgi network (TGN) since syntaxin 6 is localized mainly to this organelle (Klumperman et al., 1998a; Bock et al., 1996) and has been implicated in the clathrin-coated vesicle trafficking from the TGN to endosomes (Bock et al., 1997). Most interestingly, γ(40)- and γ(42)-secretase activity were not separable as demonstrated by an identical co-distribution across the entire gradient.

EXAMPLE 2

A screening procedure to identify compounds which modulate γ-secretase cleavage specificity and can be of use for treatment of Alzheimer's disease.

Methods

Membrane Preparation from Human SH-SY5Y Neuroblastoma or Other Cell Culture Cell Lines Membranes from human SH-SY5Y neuroblastoma cells were prepared essentially as described previously (Beher et al., 2001). Briefly, after collection in phosphate buffered saline (PBS), 2 mM EDTA cells were hypotonically shocked by incubation for 8 min in 20 mM HEPES-HCl, pH 7.3, 10 mM KCl and sedimented by centrifugation for 10 min at 1,000 g. Cells were homogenized in 20 mM HEPES-HCl, pH 7.3, 90 mM KCl and nuclei and cellular debris removed by centrifugation for 10 min at 1,000 g. Cellular membranes were sedimented by centrifugation for 1 h at 45,000 rpm (50.2 Ti rotor, Beckman), resuspended in PBS, 5% glycerol and stored at −80° C. prior to further use.

Membrane Preparation from Rodent or Guinea Pig Brain

Forebrains were prepared immediately after culling the animals and homogenized in 10 volumes of Sol A (320 mM sucrose, 5 mM HEPES-HCl, pH 7.3) using a Dounce glass homogenizer with a Teflon pestle. Nuclei and cellular debris were removed by centrifugation for 10 min at 800 g. The supernatant was collected and the pellet re-homogenized in 2 volumes of Sol A and the centrifugation step was repeated. Both supernatants were combined and the membranes sedimented by centrifugation for 1 h at 50,000 rpm (50.2 Ti rotor, Beckman). The membrane pellet was resuspended in PBS, 5% glycerol and stored at −80° C. prior to further use.

CHAPSO-Solubilization of Active γ-Secretase and Inhibitor Affinity Precipitations SH-SY5Y or alternative membranes (such as rodent brain membranes) stored in PBS, 5% glycerol were collected by centrifugation for 30 min at 180,000 g. Membrane proteins were solubilized in 1% (w/v) CHAPSO, 50 mM MES-NaOH, pH 6.0, 0.15 M NaCl, 5 mM $MgCl_2$, 1×EDTA-free protease inhibitor mixture (Roche Molecular Biochemicals). Insoluble debris was removed by centrifugation at 180,000 g for 30 min and the resulting supernatant (solubilized γ-secretase) adjusted with the same buffer without CHAPSO to give a final detergent concentration of 0.5% CHAPSO (w/v). Endogenous biotinylated proteins were removed by adding streptavidin-coupled magnetic beads and centrifugation for 2 min at 4,000 g after an incubation for 30 min at 4° C. For specific capture the pre-cleared solubilized preparation (1.8 ml; 0.6–0.7 mg/ml protein) was incubated for 2 h at room temperature with the biotinylated aspartyl transition state analogue inhibitor Merck C (routinely at 100 nM final concentration). To test compounds for the desired property of selectively lowering Aβ(x-42) or competition with the affinity ligand (such as γ-secretase inhibitors) these were added at various concentrations to the samples containing the biotinylated aspartyl transition state analogue inhibitor Merck C. Non-specific binding was analyzed either by adding a 100-fold excess of the non-biotinylated inhibitor Merck A or by omitting the affinity ligand.

γ-Secretase-inhibitor complexes were captured by addition of 250 μl (10 mg/ml) of streptavidin-coupled magnetic beads (Dynal) and incubation for 0.5 h at room temperature. Enzyme-inhibitor complexes were precipitated by centrifugation, the beads washed three times with corresponding buffer (0.5% CHAPSO) and subjected to immunoblotting as described (Beher et al., 2001) after addition of SDS-PAGE sample buffer. Note that routinely the precipitate was split into three samples for Western blot analysis. By considering these individual samples as 100%, the precipitate (100%) was compared to 2.5% of either the input before capture or the remaining unbound fraction after capture.

Analysis of Enhanced Binding of γ-Secretase to the Affinity Ligand or Binding Competition Using Plasmon Surface Resonance BIACORE® (Surface Plasmon Resonance Instrument)

γ-Secretase was solubilized from a membrane preparation as a preferred source and endogenous biotinylated proteins were removed by adding streptavidin-coupled magnetic beads as described for the affinity precipitations. For the actual experiments two set-ups were considered:

a) The sensor chip SA (which has a carboxymethylated dextran matrix that is pre-immobilized with streptavidin) was precoated with the affinity ligand; solubilized γ-secretase was preincubated with either of the test compounds and injected onto the chip surface. Prototypical y-secretase inhibitors decrease the total binding (seen by decrease of the total resonance units) whereas selective Aβ(x-42)-lowering compounds increase the total binding at certain concentrations when compared to the vehicle control.

b) Solubilized-secretase was pre-incubated with the affinity ligand in the presence of either of test compounds or the vehicle. The pre-formed enzyme-inhibitor complexes were injected onto the sensor chip SA surface and the binding kinetics analyzed. Prototypical γ-secretase inhibitors decrease the total binding (decrease of the total resonance units) whereas selective Aβ(x-42)-lowering compounds increase the total binding at certain concentrations compared to the vehicle control.

FIGURE LEGENDS

FIG. 1. γ-Secretase inhibitors synthesized for this study and their potencies for inhibition of γ(40)- and γ(42)-secretase activities. $IC_{50}$ values for Merck A and Merck B for inhibition of the in vitro generation of A, Aβ(40) and B, Aβ(42) in the exogenous substrate assay utilizing SH-SY5Y membranes as source of γ-secretase enzyme and recombinant C100Flag as substrate. Note that the assay is performed in the presence of 0.5% CHAPSO which is the optimum detergent concentration for γ-secretase activity in these membranes (D. Beher, unpublished observation). The reduction of Aβ generation was measured relative to $Me_2SO$-treated controls and error bars indicate the standard error the mean from triplicate experiments.

FIG. 2. Affinity capture of PS1 heterodimer and nicastrin by the biotinylated inhibitor Merck C. A, solubilized γ-secretase from SH-SY5Y membranes was incubated with increasing concentrations of the biotinylated affinity ligand Merck C and precipitated with a constant amount of streptavidin-coupled beads (0.5 mg beads). CHAPSO-solubilized membranes before ligand addition (Input: 2.5% of total) were compared to the captured fraction (Bound: 100% of total) and the corresponding supernatant after capture (Unbound: 2.5% of total) by Western blot analysis. Individual polypeptides were immunostained as indicated. B, solubilised γ-secretase from SH-SY5Y membranes was incubated with different concentrations of the affinity ligand (0.1 μM and 0.5 μM as indicated) and precipitated with increasing amounts of streptavidin-coupled beads (0.5 mg and 2.5 mg of beads, respectively). Again, CHAPSO-solubilized membranes before ligand addition (Input: 2.5% of total) were compared to the captured fraction (Bound: 100% of total) and the corresponding supernatant after capture (Unbound: 2.5% of total) by Western blot analysis. Individual polypeptides were immunostained as indicated.

FIG. 3. The binding of PS1 heterodimer and nicastrin to the biotinylated affinity probe is competed by the non-biotinylated inhibitor Merck A. A, solubilized γ-secretase from SH-SY5Y membranes was incubated with 0.1 μM of the affinity ligand Merck C in the absence or presence of a 100-fold excess (10 μM) of Merck A and precipitated with streptavidin-coupled beads (2.5 mg). CHAPSO-solubilized membranes before ligand addition (Input: 2.5% of total) were compared to the captured fraction in the presence (Bound non-spec.: 100% of total) or absence (Bound spec.: 100% of total) of the competing inhibitor Merck A and the corresponding supernatants after capture (Unbound non-spec. and Unbound spec.: 2.5% of total) by Western blot analysis. Individual polypeptides were immunostained as indicated. In the presence of a 100-fold excess of competing inhibitor Merck A the precipitation of the PS1 heterodimer and nicastrin is abolished. β-catenin, however, is not captured under any condition. B, solubilised γ-secretase from SH-SY5Y membranes was incubated with 0.1 μM of the affinity ligand Merck C and precipitated with streptavidin-coupled beads (2.5 mg). CHAPSO-solubilized membranes before ligand addition (Input: 2.5% of total) were compared to the specifically captured fraction (Bound spec.: 100% of total) by Western blot analysis after an extended gel run. A clear separation of mature and immature nicastrin polypeptides is visible in the input and only the band with a higher Mr representing mature nicastrin is captured by the affinity ligand.

Figure 4:
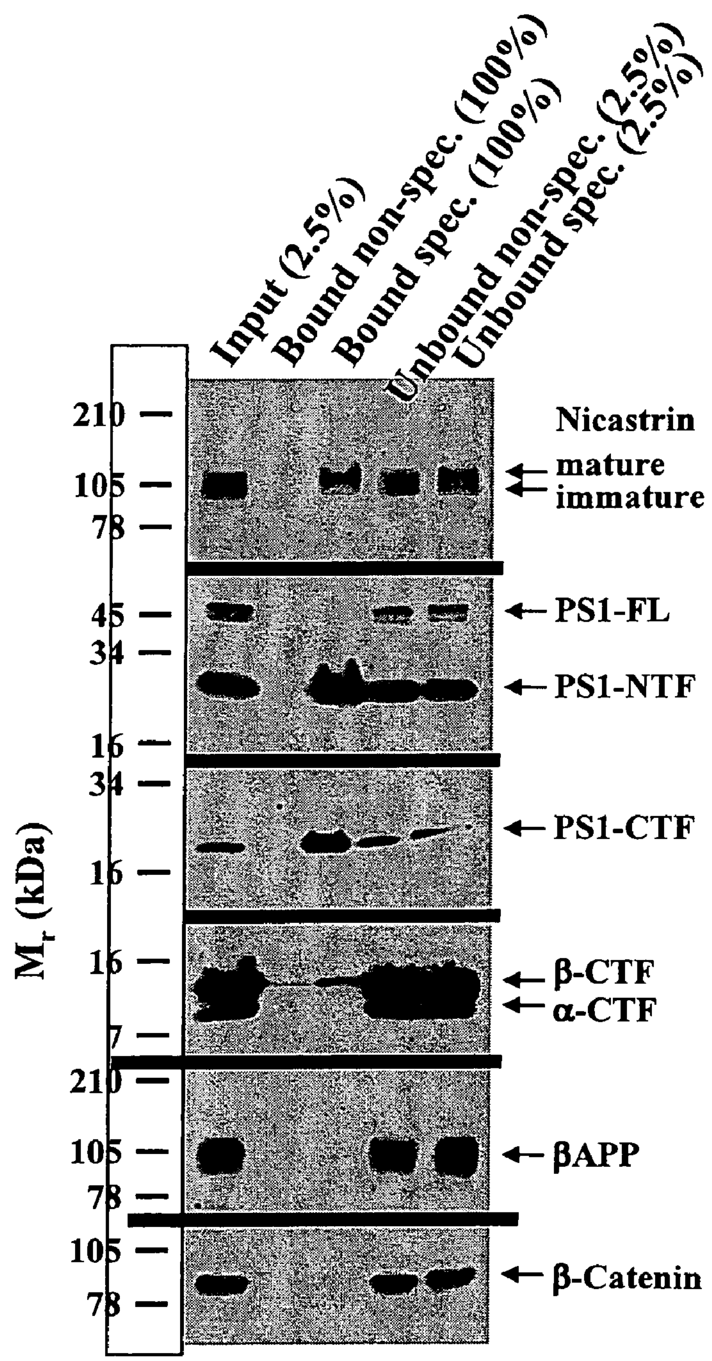
Figure 5C:
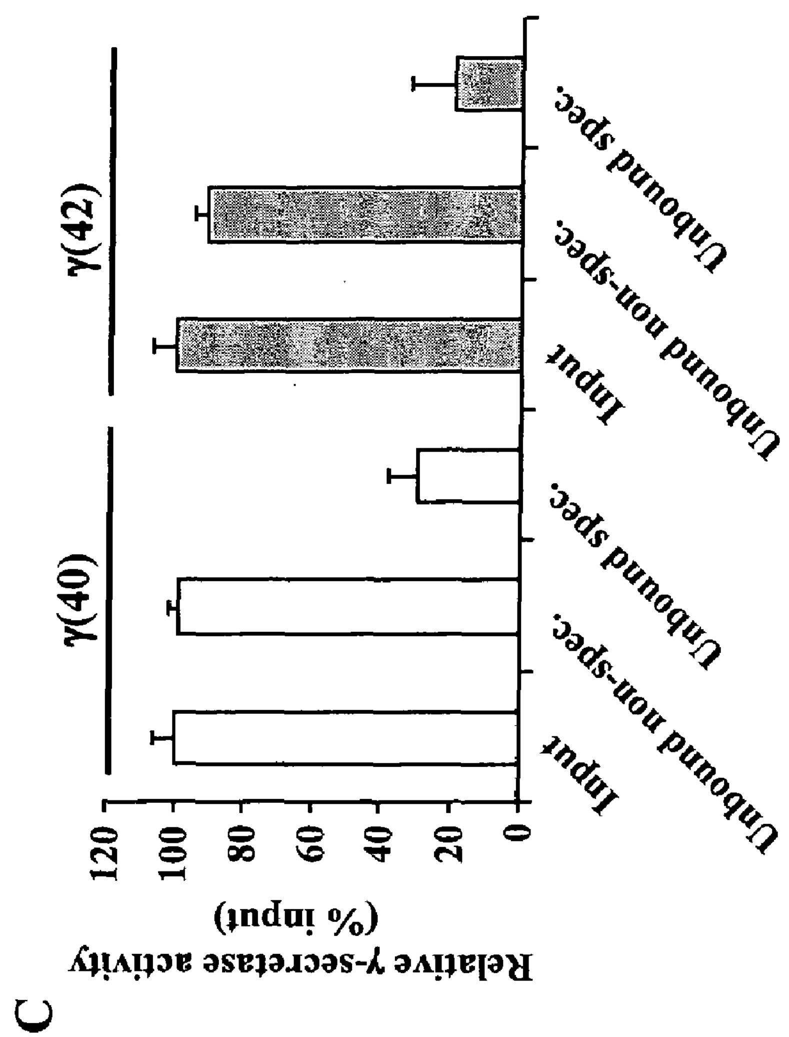

FIG. 4. Simultaneous binding of the substrate and a transition state analogue inhibitor to γ-secretase. γ-Secretase was solubilized using membranes prepared from SH-SY5Y cells stably over-expressing a γ-secretase substrate β-CTF (C99) variant. The solubilized membranes were incubated either in the presence of Merck A or the affinity probe Merck C (0.1 μM each) followed by precipitation with streptavidin-coupled beads (2.5 mg). Merck A was added to the control sample without the affinity ligand to ensure that both samples contain a γ-secretase inhibitor as a precaution to prevent any turnover of the β-CTF by γ-secretase. Solubilized membranes before ligand addition (Input: 2.5% of total) were compared to the captured fraction in the absence (Bound non-spec.: 100%) or presence (Bound spec.: 100% of total) of the affinity ligand and the corresponding supernatants after capture (Unbound non-spec. and Unbound spec.: 2.5% of total each) by Western blot analysis. Individual polypeptides were immunostained as indicated.

FIG. 5. Quantitation of the depletion of γ-secretase activity from solubilized membranes by binding to the biotinylated affinity probe. Solubilized γ-secretase from SH-SY5Y membranes was incubated A, in the presence (0.1 μM; +Affinity ligand) or B, absence of the biotinylated affinity ligand Merck C (−Affinity ligand). For capture of γ-secretase and free ligand, streptavidin-coupled beads (2.5 mg) were added eight times repeatedly (without any further affinity ligand addition). For each individual streptavidin-bead addition, a 30 min capture incubation was followed by subsequent precipitation of the beads by centrifugation. The resulting supernatant was subjected to the next repeated streptavidin bead capture and the corresponding bead pellet washed three times in CHAPSO-buffer. A, solubilized γ-secretase before ligand addition (Input: 2.5% of total) and corresponding supernatants after eight repeated bead captures in the absence (Unbound non-spec.: 2.5% of total) or original presence of the affinity ligand (Unbound spec.: 2.5% of total) were compared by Western blot analysis. Polypeptides captured by each individual bead addition (100% of total: +Affinity ligand) are shown as indicated. B, the results of the corresponding experiment performed in the absence of the affinity ligand are shown. Solubilized γ-secretase before ligand addition (Input: 2.5% of total) and corresponding supernatants after eight repeated bead captures in the absence (Unbound non-spec.: 2.5% of total) or original presence of the affinity ligand (Unbound spec.: 2.5% of total) were compared to the material captured by each individual bead addition in total absence of the affinity ligand (100% of total: −Affinity ligand). C, γ(40)- and γ(42)-secretase activities present in the solubilized membranes before ligand addition (Input) and after eight repeated bead captures in the absence (Unbound non-spec.) or original presence of the affinity ligand (Unbound spec.) were compared using an exogenous substrate assay (10 μg C100Flag, 40 μl of solubilized enzyme each reaction). The samples used for this assay were from the same experiments shown in A and B. Error bars indicate the standard error of the measurements obtained from quadruplicate in vitro reactions. The results shown in A–C are representative of three independent experiments.

Figure 6:
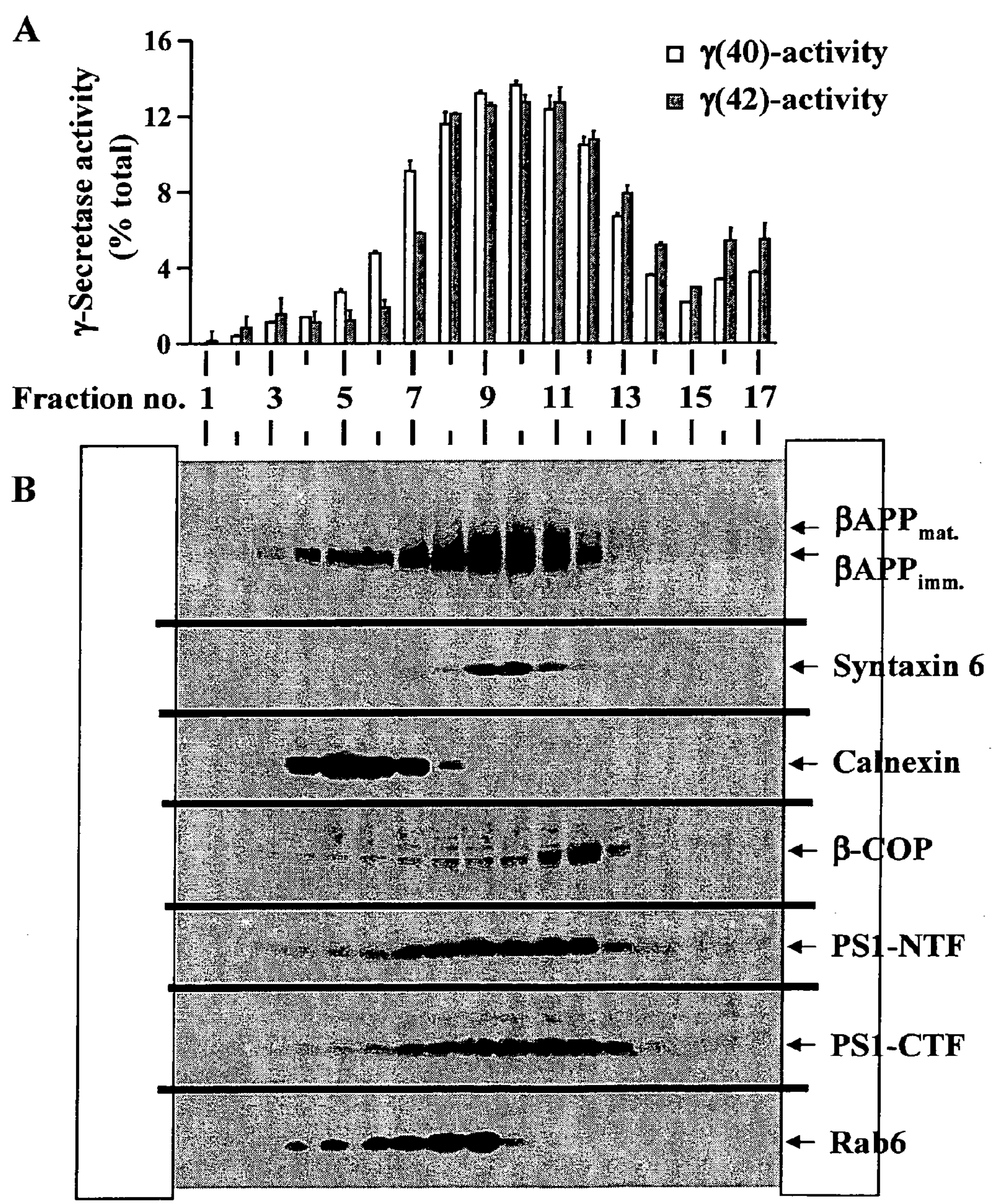

FIG. 6 Subcellular fractionation of γ-secretase. Membranous organelles from SH-SY5Y cells were separated by sucrose density gradient centrifugation. A, equal aliquots of individual fractions were analyzed for γ(40)- and γ(42)-secretase activities using an exogenous substrate assay and the relative enzyme activity in each fraction was plotted in the graph. B, equal aliquots of the same fractions were immunoblotted for individual polypeptides as indicated. The graph in A shows the average of duplicate measurements and the data shown in A and B is representative of three independent experiments. The box highlights four fractions containing the highest γ(40)- and γ(42)-secretase activities (fractions 8–11).

Figure 7:
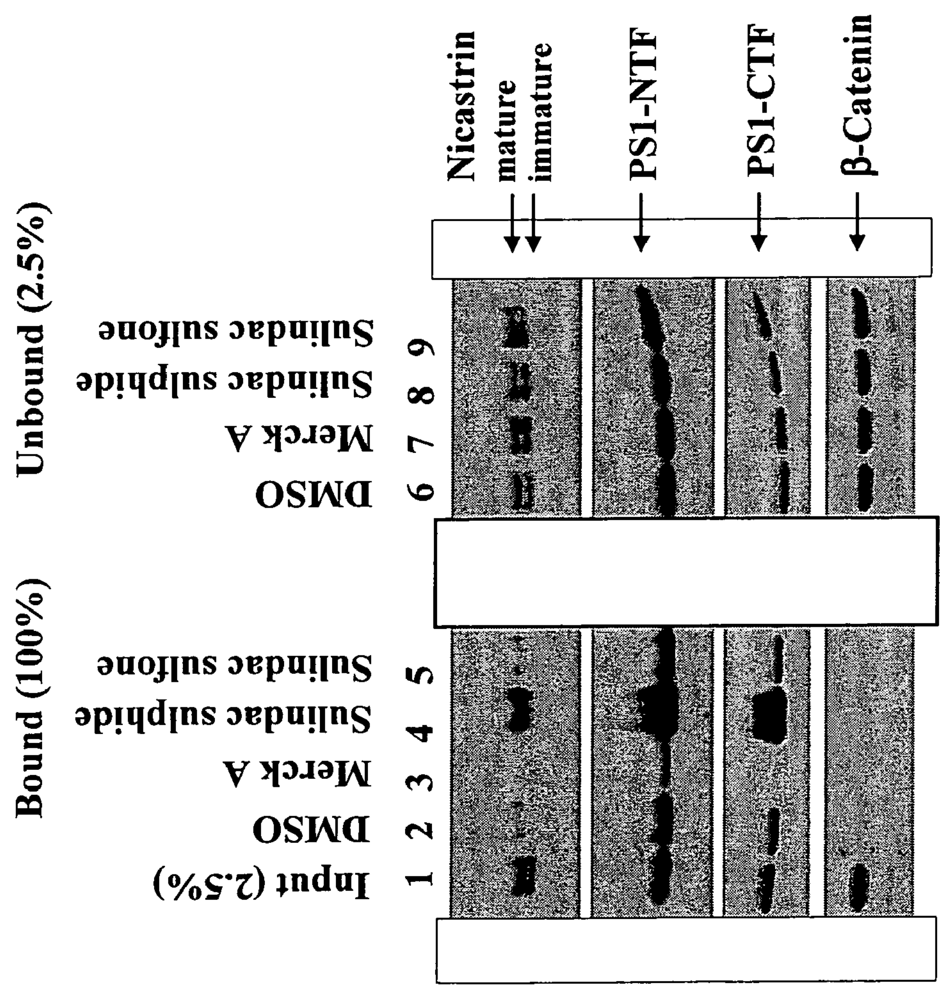

FIG. 7. The binding of the PS1 heterodimer and nicastrin to the biotinylated affinity probe is enhanced by the selectively Aβ(x-42)-lowering compound sulindac sulphide. Solubilized γ-secretase from SH-SY5Y membranes was incubated with 0.1 μM of the affinity ligand Merck C in the absence or presence of 200 μM of either sulindac sulphide or sulindac sulfone or a 100-fold excess (10 μM) of Merck A and precipitated with streptavidin-coupled beads (2.5 mg). CHAPSO-solubilized membranes before ligand addition (Input: 2.5% of total) were compared to the captured fraction in the presence (Bound non-spec.: 100% of total) or absence (Bound spec.: 100% of total) of either sulindac sulphide or sulindac sulfone or the competing inhibitor Merck A and the corresponding supernatants after capture (Unbound non-spec. and Unbound spec.: 2.5% of total) by Western blot analysis. Individual polypeptides were immunostained as indicated. In the presence of a 100-fold excess of competing prototypical γ-secretase inhibitor Merck A the precipitation of the PS1 heterodimer and mature nicastrin is abolished. This is seen with other structurally diverse true γ-secretase inhibitors as well (data not shown) and demonstrates that this method can be used to identify inhibitors of γ-secretase. Note that β-catenin, is not captured under any condition, which serves as a control for non-specific binding to the streptavidin-coupled beads. In the presence of the selectively Aβ(x-42)-lowering compound sulindac sulphide the overall capture efficiency for the PS1 heterodimer and mature nicastrin is enhanced as seen by stronger immunoreactivities for the respective polypeptides. In contrast upon addition of sulindac sulfone, a closely related analogue which does not lower Aβ(x-42) production the capture is comparable to the DMSO ($Me_2O$) control. This finding demonstrates that the method described herein can be used to identify selectively Aβ(x-42)-lowering compounds. The abbreviations used are: AD, Alzheimer's disease; βAPP, β-amyloid precursor protein; Aβ, amyloid-β peptide; CHAPSO, 3-[(3-cholamidopropyl)dimethylammonio]-2-hydroxy-1-propanesulfonate; DCM, dichloromethane; DMF, N,N-dimethylformamide; DMSO, dimethyl sulfoxide; ECL, electrochemiluminescence; EDC, 1-(3-dimethylaminopropyl)-3-ethylcarbodiimide hydrochloride; ER, endoplasmic reticulum; HOBT, 1-hydroxybenzotriazole hydrate; MES, 2-[N-Morpholino]ethanesulfonic acid; TBAF, tetrabutylammonium fluoride; TFA, trifluoroacetic acid; TGN, trans-Golgi network; THF, tetrahydrofuran; PS1/2, presenilin ½; PS1-FL, full-length presenilin 1; NTF, N-terminal fragment; CTF, C-terminal fragment; PAGE, polyacrylamide gel electrophoresis; SAR, structure-activity relationship; SDS, sodium dodecyl sulphate; PBS, phosphate-buffered saline.

REFERENCES

1. Antony C, Cibert C, Geraud. G, Santa M A, Maro B, Mayau V, Goud B (1992) The small GTP-binding protein rab6p is distributed from medial Golgi to the trans-Golgi network as determined by a confocal microscopic approach. J Cell Sci 103 (Pt 3): 785–796.
2. Beher D, Elle C, Underwood J, Davis J B, Ward R, Karran E, Masters C L, Beyreuther K, Multhaup G (1999) Proteolytic fragments of Alzheimer's disease-associated presenilin 1 are present in synaptic organelles and growth cone membranes of rat brain. J Neurochem 72: 1564–1573.
3. Beher D, Wrigley J D, Nadin A, Evin G, Masters C L, Harrison T, Castro J L, Shearman M S (2001) Pharmacological knock-down of the presenilin 1 heterodimer by a novel gamma-secretase inhibitor: implications for presenilin biology. J Biol Chem 276: 45394–45402.
4. Bock J B, Klumperman J, Davanger S, Scheller R H (1997) Syntaxin 6 functions in trans-Golgi network vesicle trafficking. Mol Biol Cell 8: 1261–1271.
5. Bock J B, Lin R C, Scheller R H (1996) A new syntaxin family member implicated in targeting of intracellular transport vesicles. J Biol Chem 271: 17961–17965.
6. Culvenor J G, Evin G, Cooney M A, Wardan H, Sharples R A, Maher F, Reed G, Diehlmann A, Weidemann A, Beyreuther K, Masters C L (2000) Presenilin 2 expression in neuronal cells: induction during differentiation of embryonic carcinoma cells. Exp Cell Res 255: 192–206.
7. Dyrks T, Dyrks E, Monning U, Urmoneit B, Turner J, Beyreuther K (1993) Generation of beta A4 from the amyloid protein precursor and fragments thereof. FEBS Lett 335: 89–93.
8. Esler W P, Kimberly W T, Ostaszewski B L, Ye W, Diehl T S, Selkoe D J, Wolfe M S (2002) Activity-dependent isolation of the presenilin-gamma-secretase complex reveals nicastrin and a gamma substrate. Proc Natl Acad Sci U S A 99: 2720–2725.
9. Esler W P, Wolfe M S (2001) A portrait of Alzheimer secretases—new features and familiar faces. Science 293: 1449–1454.
10. Evin G, Sharples R A, Weidemann A, Reinhard F B, Carbone V, Culvenor J G, Holsinger R M, Sernee M F, Beyreuther K, Masters C L (2001) Aspartyl protease inhibitor pepstatin binds to the presenilins of alzheimer's disease. Biochemistry 40: 8359–8368.
11. Fortini M E (2002) Signalling: gamma-Secretase-mediated proteolysis in cell-surface-receptor signalling. Nat Rev Mol Cell Biol 3: 673–684.
12. Francis R, McGrath G, Zhang J, Ruddy D A, Sym M, Apfeld J, Nicoll M, Maxwell M, Hai B, Ellis M C, Parks A L, Xu W, Li J, Gurney M, Myers R L, Himes C S, Hiebsch R, Ruble C, Nye J S, Curtis D (2002) aph-1 and pen-2 are required for Notch pathway signaling, gamma-secretase cleavage of betaAPP, and presenilin protein accumulation. Dev Cell 3: 85–97.
13. Girod A, Storrie B, Simpson J C, Johannes L, Goud B, Roberts L M, Lord J M, Nilsson T, Pepperkok R (1999) Evidence for a COP-I-independent transport route from the Golgi complex to the endoplasmic reticulum. Nat Cell Biol 1: 423–430.
14. Goud B, Zahraoui A, Tavitian A, Saraste J (1990) Small GTP-binding protein associated with Golgi cisternae. Nature 345: 553–556.
15. Griffiths G, Pepperkok R, Locker J K, Kreis T E (1995) Immunocytochemical localization of beta-COP to the ER-Golgi boundary and the TGN. J Cell Sci 108 (Pt 8): 2839–2856.
16. Hardy J, Selkoe D J (2002) The amyloid hypothesis of Alzheimer's disease: progress and problems on the road to therapeutics. Science 297: 353–356.
17. Kimberly W T, LaVoie M J, Ostaszewski B L, Ye W, Wolfe M S, Selkoe D J (2002) Complex N-linked Glycosylated Nicastrin Associates with Active gamma-Secretase and Undergoes Tight Cellular Regulation. J Biol Chem 277: 35113–35117.
18. Klumperman J, Kuliawat R, Griffith J M, Geuze H J, Arvan P (1998a) Mannose 6-phosphate receptors are sorted from immature secretory granules via adaptor protein AP-1 clathrin, and syntaxin 6-positive vesicles. J Cell Biol 141: 359–371.

19. Klumperman J, Schweizer A, Clausen H, Tang B L, Hong W, Oorschot V, Hauri H P (1998b) The recycling pathway of protein ERGIC-53 and dynamics of the ER-Golgi intermediate compartment. J Cell Sci 111 (Pt 22): 3411–3425.

20. Lee S F, Shah S, Li H, Yu C, Han W, Yu G (2002) Mammalian APH-1 interacts with presenilin and nicastrin, and is required for intramembrane proteolysis of APP and Notch. J Biol Chem.

21. Leem J Y, Vijayan S, Han P, Cai D, Machura M, Lopes K O, Veselits M L, Xu H, Thinakaran G (2002) Presenilin 1 is required for maturation and cell surface accumulation of nicastrin. J Biol Chem 277: 19236–19240.

22. Li Y M, Lai M T, Xu M, Huang Q, DiMuzio-Mower J, Sardana M K, Shi X P, Yin K C, Shafer J A, Gardell S J (2000a) Presenilin 1 is linked with gamma-secretase activity in the detergent solubilized state. Proc Natl Acad Sci U S A 97: 6138–6143.

23. Li Y M, Xu M, Lai M T, Huang Q, Castro J L, DiMuzio-Mower J, Harrison T, Lellis C, Nadin A, Neduvelil J G, Register R B, Sardana M K, Shearman M S, Smith A L, Shi X P, Yin K C, Shafer J A, Gardell S J (2000b) Photoactivated g-secretatase inhibitors directed to the active site covalently label presenilin 1. Nature 405: 689–694.

24. Martinez O, Schmidt A, Salamero J, Hoflack B, Roa M, Goud B (1994) The small GTP-binding protein rab6 functions in intra-Golgi transport. J Cell Biol 127: 1575–1588.

25. Nadin A, Sanchez Lopez J M, Neduvelil J G, Thomas S R (2001) A stereocontrolled synthesis of 2R-benzyl-5S-tert-butoxycarbonylamino-4R-(tert-butyldimethylsilanyloxy)-6-phenyl-hexanoic acid (Phe-Phe hydroxyethylene dipeptide isostere). Tetrahedron 57: 1861–1864.

26. Pepperkok R, Scheel J, Horstmann H, Hauri H P, Griffiths G, Kreis T E (1993) Beta-COP is essential for biosynthetic membrane transport from the endoplasmic reticulum to the Golgi complex in vivo. Cell 74: 71–82.

27. Rogaev E I, Sherrington R, Rogaeva E A, Levesque G, Ikeda M, Liang Y, Chi H, Lin C, Holman K, Tsuda T (1995) Familial Alzheimer's disease in kindreds with missense mutations in a gene on chromosome 1 related to the Alzheimer's disease type 3 gene. Nature 376: 775–778.

28. Shearman M S, Beher D, Clarke E E, Lewis H D, Harrison T, Hunt P, Nadin A, Smith A L, Stevenson G, Castro J L (2000) L-685,458, an aspartyl protease transition state mimic, is a potent inhibitor of amyloid b-protein precursor g-secretase activity. Biochemistry 38: 8698–8704.

29. Shen J, Bronson R T, Chen D F, Xia W, Selkoe D J, Tonegawa S (1997) Skeletal and CNS defects in Presenilin-1-deficient mice. Cell 89: 629–639.

30. Sherrington R, Rogaev E I, Liang Y, Rogaeva E A, Levesque G, Ikeda M, Chi H, Lin C, Li G, Holman K (1995) Cloning of a gene bearing missense mutations in early-onset familial Alzheimer's disease. Nature 375: 754–760.

31. Steiner H, Winkler E, Edbauer D, Prokop S, Basset G, Yamasaki A, Kostka M, Haass C (2002) PEN-2 is an integral component of the gamma-secretase complex required for coordinated expression of presenilin and nicastrin. J Biol Chem.

32. Thinakaran G, Borchelt D R, Lee M K, Slunt H H, Spitzer L, Kim G, Ratovitsky T, Davenport F, Nordstedt C, Seeger M, Hardy J, Levey A I, Gandy S E, Jenkins N A, Copeland N G, Price D L, Sisodia S S (1996) Endoproteolysis of presenilin 1 and accumulation of processed derivatives in vivo. Neuron 17: 181–190.

33. Weggen S, Eriksen J L, Das P, Sagi S A, Wang R, Pietrzik C U, Findlay K A, Smith T E, Murphy M P, Bulter T, Kang D E, Marquez-Sterling N, Golde T E, Koo E H (2001) A subset of NSAIDs lower amyloidogenic Abeta42 independently of cyclooxygenase activity. Nature 414: 212–216.

34. White J, Johannes L, Mallard F, Girod A, Grill S, Reinsch S, Keller P, Tzschaschel B, Echard A, Goud B, Stelzer E H (1999) Rab6 coordinates a novel Golgi to ER retrograde transport pathway in live cells. J Cell Biol 147: 743–760.

35. Wolfe M S, Xia W, Ostaszewski B L, Diehl T S, Kimberly W T, Selkoe D J (1999) Two transmembrane aspartates in presenilin-1 required for presenilin endoproteolysis and gamma-secretase activity. Nature 398: 513–517.

36. Wong P C, Zheng H, Chen H, Becher M W, Sirinathsinghji D J, Trumbauer M E, Chen H Y, Price D L, Van der Ploeg L H, Sisodia S S (1997) Presenilin 1 is required for Notch1 and DII1 expression in the paraxial mesoderm. Nature 387: 288–292.

37. Yang D S, Tandon A, Chen F, Yu G, Yu H, Arawaka S, Hasegawa H, Duthie M, Schmidt S D, Ramabhadran T V, Nixon R A, Mathews P M, Gandy S E, Mount H T, George-Hyslop P, Fraser P E (2002) Mature glycosylation and trafficking of nicastrin modulate its binding to presenilins. J Biol Chem 277: 28135–28142.

38. Yu G, Nishimura M, Arawaka S, Levitan D, Zhang L, Tandon A, Song Y Q, Rogaeva E, Chen F, Kawarai T, Supala A, Levesque L, Yu H, Yang D S, Holmes E, Milman P, Liang Y, Zhang D M, Xu D H, Sato C, Rogaev E, Smith M, Janus C, Zhang Y, Aebersold R, Farrer L S, Sorbi S, Bruni A, Fraser P, George-Hyslop P (2000) Nicastrin modulates presenilin-mediated notch/glp-1 signal transduction and betaAPP processing. Nature 407: 48–54.

The invention claimed is:

1. An assay for identifying a test compound which interacts with the γ-secretase complex, and which would reduce the production of Aβ42 by the gamma secretase complex in vivo, said gamma secretase complex comprising PS1-NTF, PS1-CTF, and mature nicastrin, wherein the assay comprises the steps of:

preparing a biochemical source of the γ-secretase complex;

solubilizing the source;

incubating the source and an affinity probe to form a first composition;

incubating the source and an affinity probe and a test compound to form a second composition under the same incubating conditions for the first composition;

capturing the gamma secretase complex bound to the affinity probe in the first and second compositions;

determining the amount of PS1-NTF, PS1-CTF or mature nicastrin bound to the affinity probe in the first and second compositions;

identifying a test compound that increases the level of binding of the affinity probe to PS1-NTF, PS1-CTF or mature nicastrin relative to the level of binding of the affinity probe to PS-1-NTF, PS1-CTF or mature nicastrin in the first composition;

thereby identifying a test compound which interacts with the γ-secretase complex in a manner which would reduce the production of Aβ42 by the gamma secretase complex in vivo.

2. An assay according to claim 1 wherein the amounts of two or more of the bound components PS1-CTF, PS1-NTF and mature nicastrin determined.

3. An assay according to claim 1, further comprising determining the amount of PEN-2 bound to the affinity probe in the first and second compositions.

4. An assay according to claim 1, further comprising determining the amount of APH-1 bound to the affinity probe in the first and second compositions.

5. An assay according to claim 1 wherein the biochemical source of the γ-secretase complex is a membrane fraction of HEK cells, human SH-SY5Y neuroblastoma cells or rodent brain.

6. An assay according to claim 1 wherein the biochemical source of the γ-secretase complex is derived from cells or animals genetically transformed to over express one or more known components of the γ-secretase complex.

7. An assay according to claim 1 wherein the γ-secretase complex is partially purified.

8. An assay according to claim 1 wherein the source is solubilized in CHAPSO.

9. An assay according to claim 8 wherein the solubilization occurs in 1% CHAPSO which is diluted to 0.5% prior to the incubation step.

10. An assay according to claim 1 wherein the probe is biotinylated.

11. An assay according to claim 10 wherein the affinity probe is

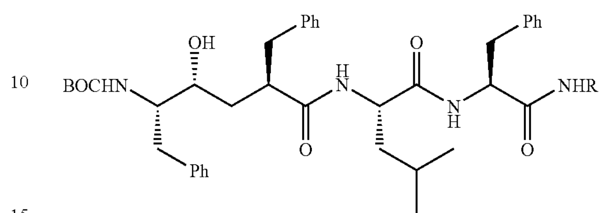

wherein $R=(CH_2)_5[NHCO(CH_2)_5]_3NHCO(CH_2)_2SS(CH_2)_2NHBiotin$.

12. An assay according to claim 10 wherein the probe is captured using streptavidin beads.

13. An assay according to claim 1 wherein the determining step is carried out using Western blotting.

* * * * *